United States Patent
Annett et al.

(10) Patent No.: US 6,863,071 B2
(45) Date of Patent: Mar. 8, 2005

(54) REFRACTIVE SURGICAL DRAPE

(75) Inventors: Leland W. Annett, Stillwater, MN (US); David B. Padget, Stillwater, MN (US)

(73) Assignee: Medical Concepts Development, Inc., St. Paul, MN (US)

( * ) Notice: Subject to any disclaimer, the term of this patent is extended or adjusted under 35 U.S.C. 154(b) by 151 days.

(21) Appl. No.: 10/190,984

(22) Filed: Jul. 3, 2002

(65) Prior Publication Data

US 2004/0003817 A1 Jan. 8, 2004

(51) Int. Cl.$^7$ .............................................. A61B 19/00
(52) U.S. Cl. ........................ 128/849; 128/853; 128/854
(58) Field of Search ................................. 128/849, 853, 128/854, 850; 2/410, 424, 15, 9, 206

(56) References Cited

U.S. PATENT DOCUMENTS

| | | | | |
|---|---|---|---|---|
| 3,667,458 A | * | 6/1972 | Krebs | 128/853 |
| 4,316,455 A | * | 2/1982 | Stoneback | 128/853 |
| 4,316,456 A | * | 2/1982 | Stoneback | 128/853 |
| RE34,512 E | * | 1/1994 | Dowdy et al. | 128/853 |
| 5,345,946 A | * | 9/1994 | Butterworth et al. | 128/853 |
| 6,070,587 A | * | 6/2000 | Levitt et al. | 128/849 |
| 6,105,579 A | * | 8/2000 | Levitt et al. | 128/849 |
| 6,286,511 B1 | | 9/2001 | Levitt et al. | 128/849 |
| 6,345,621 B1 | * | 2/2002 | Chandler et al. | 128/849 |
| 6,405,730 B2 | * | 6/2002 | Levitt et al. | 128/849 |

* cited by examiner

*Primary Examiner*—Fadi H. Dahbour
(74) *Attorney, Agent, or Firm*—Nawrocki, Rooney & Sivertson, P.A.

(57) ABSTRACT

The invention comprises a surgical drape formed of a sheet material having a periphery and with a particular type of aperture spaced from periphery. The invention further comprises a method of using the drape. The aperture has a dominant portion and at least one subordinate portion. At least one subordinate portion of the aperture radially extends from the dominant portion. An adhesive layer may underlie an area surrounding the aperture.

22 Claims, 3 Drawing Sheets

REFRACTIVE SURGICAL DRAPE

TECHNICAL FIELD

The present invention relates generally to surgical drapes and methods of applying same, and more particularly to apertured surgical drapes, especially those utilized in ophthalmic procedures or the like, and methods of applying such drapes.

BACKGROUND OF INVENTION

Maintenance of a sterile field is critical in surgical applications. Conforming a surgical drape to the patient is of considerable importance, as evidence by the number of issued patents directed to drape configuration and arrangement, let alone the number of commercially available drapes.

In ophthalmic procedures, it is advantageous to apply a surgical drape which permits isolation of the eye lashes and eyelids from the surgical site in furtherance of exposure of the eye, and provides a sterile drape surface to minimize infection at the site. Such is the case in refractive surgery wherein draping may be primarily performed to retract the eyelids and lashes from the surface of the eye, thereby keeping those structures clear of surgical instruments such as microkeratomes. As practitioners have come to learn, manipulation of eye structures in furtherance of ophthalmic surgery, while maintaining a sterile field, is not without its inherent and practical difficulties.

As the eye is a delicate structure, with the eyelids being very flexible and of unique configuration and dimension from one patient to the next, practitioners find it inconvenient and challenging to conform the margins of the aperture to the edges of a particular patient's eyelids. This however does not mean a one size fits all approach is taken, instead, one know technique is to cut the drape, at least partly and especially to extend outward from the aperture, prior to applying same to the patient. By doing this, tension is relieved in stressed or stretched areas (i.e., resulting from substantially conforming the aperture margins to the eye structures), and bunching of the adhesive field/layer avoided. Furthermore, cutting the drape prior to application facilitates application of the drape first, for instance, to the upper eyelid, without adhering the lower portions of the adhesive layer to the lower eyelid until ready to do so. In addition to the general inconvenience of requiring the presence of a sterile scissor or the like, making an appropriate cut while attempting to preserve drape sterility is not necessarily achievable.

In lieu of practitioners cutting the drape as they had been inclined to do, drape designers next provided drapes having tear lines extending from the aperture so as satisfy objectives of conforming the drape to the surgical site (i.e., matching the margins of the aperture to the edges of the eyelids), and facilitating sequenced placement (i.e., positioning on a first eyelid, followed by positioning on a second eyelid). Such approach is discussed in U.S. Pat. No. 6,286,511 (Levitt et al.). Furthermore, drapes have been supplied in sections (i.e., halves), with each part of the whole separately and accurately applied to the patient. Although such styles or approaches have been perceived as an improvement, both require an attention to detail than makes application of the drape more time consuming that one might imagine, especially the two-piece style, with drapes having a tear line nonetheless requiring manipulation by a practitioner (i.e., tearing). Thus there remains a need to provide an apertured surgical drape which is quickly and readily applied so as to establish and reliably maintain a sterile field about the work site.

SUMMARY OF THE INVENTION

A surgical drape including a sheet material having a periphery and an aperture spaced apart from said periphery is provided, along with an attendant methodology. The aperture has a dominant portion and at least one subordinate portion, the at least one subordinate portion radially extends from the dominant portion. More specific features and advantages will become apparent with reference to the DETAILED DESCRIPTION OF THE INVENTION, appended claims, and the accompanying drawing figures.

DETAILED DESCRIPTION OF THE INVENTION

The surgical drape of the subject invention is particularly well suited for ophthalmic procedures, but is not so limited. For instance, extremity surgeries, ear, nose or throat procedures, breast surgery, etc., are likewise contemplated. The subject invention is subsequently described in detail in the context of ophthalmic surgery.

Figure 1:
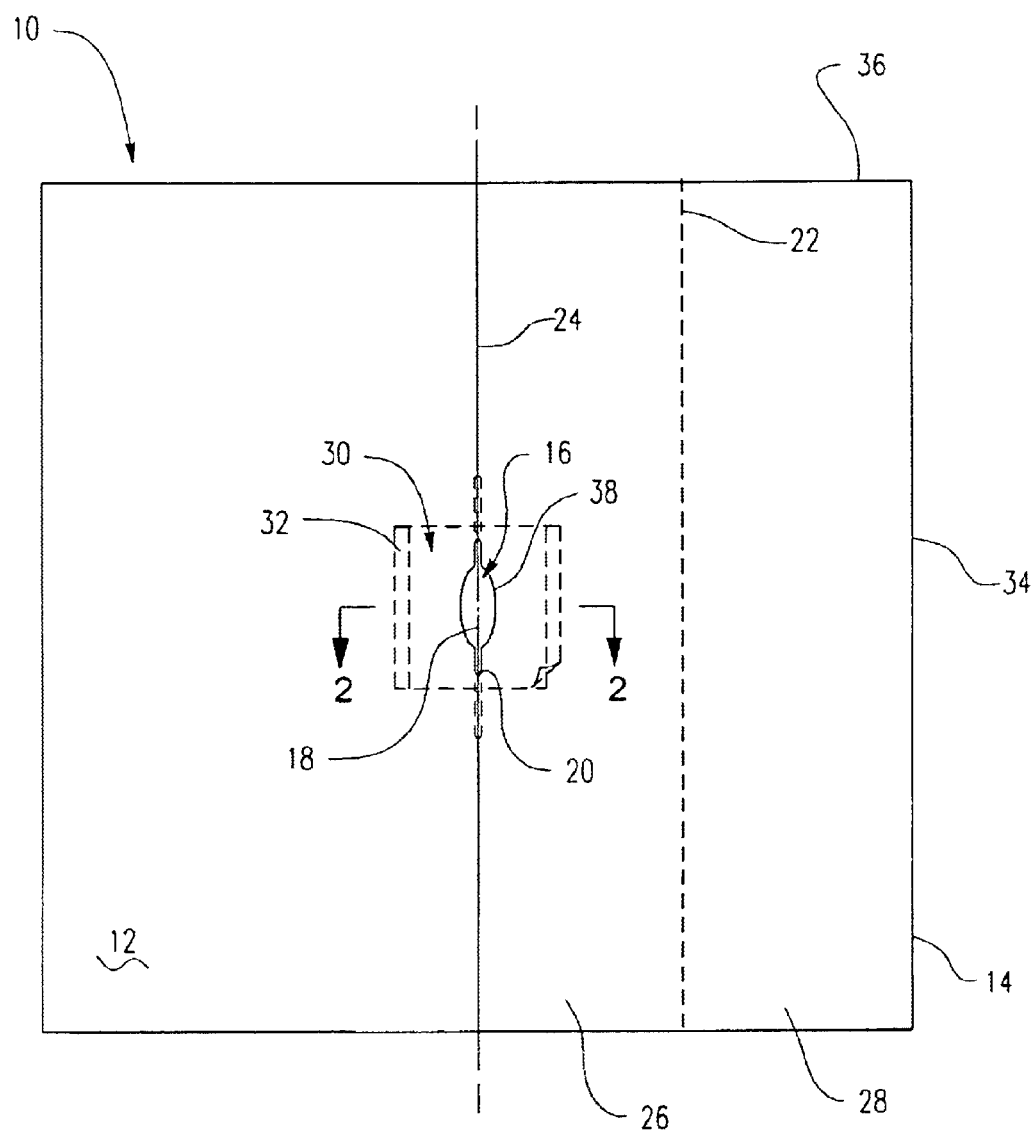
FIG. 1 is a plan view of a surgical drape of the subject invention.
Figure 2:
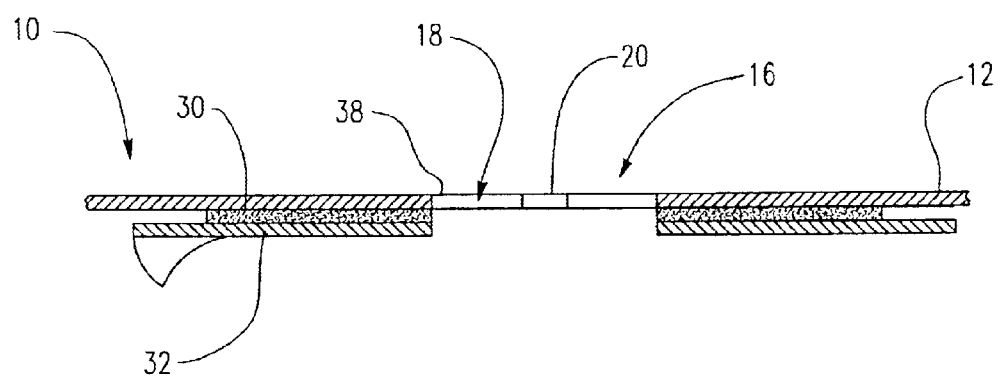
FIG. 2 is a partial cross-section view of the drape of FIG. 1 taken about line 2—2; and, FIG. 3 illustrates the drape of the subject invention in an applied condition, more particularly the primary portion, the aperture therein having a deformed margin in furtherance of sterile field establishment.

Referring to FIGS. 1 & 2, there is generally shown the surgical drape 10 of the subject invention. The drape includes a sheet material 12 having a periphery 14 and an aperture 16 spaced apart therefrom. The aperture 16, which is generally of an elongate character, has a dominant portion 18, and at least a single subordinate portion 20 radially extending from the dominant portion 18. As shown in the figures, the aperture 16 preferably, but not necessarily, includes opposingly paired subordinate aperture portions.

In the embodiment shown, the sheet material 12 of the drape 10 includes a line of weakness 22 extending substantially parallel to an axis of elongation 24 of the aperture 16 so as to divide the drape 10 into primary 26 and secondary 28 portions. The sheet 12 further includes an adhesive layer 30 on a surface thereof, in the vicinity of the aperture 16, with such adhesive layer 30 being well know to those of skill in the surgical drape art. The adhesive 30 generally surrounds the aperture 16 in furtherance of initially, and finally, positioning and securing the drape 10 at the surgical site, more particularly, the adhesive 30 is at least adjacent the dominant portion 18 of the aperture 16, and preferably further adjacent at least a portion of the subordinate portion 20 of the aperture 16. A release liner 32, of the form and substance generally known to those of skill in the art, generally overlays the adhesive layer 30.

The aperture 16 is preferably, but not critically, centrally located within the periphery 14 of the sheet material 12. Similarly, in the context of sheet material configured as a parallelogram, it is advantageous but not essential that the aperture 16 have its axis of elongation 24 normal to a portion of the periphery 14 (i.e., the elongate aperture 16 is substantially parallel to a first set 34 of opposing drape edges, and substantially perpendicular to a second set 36 of opposing drape edges).

Figure 3:
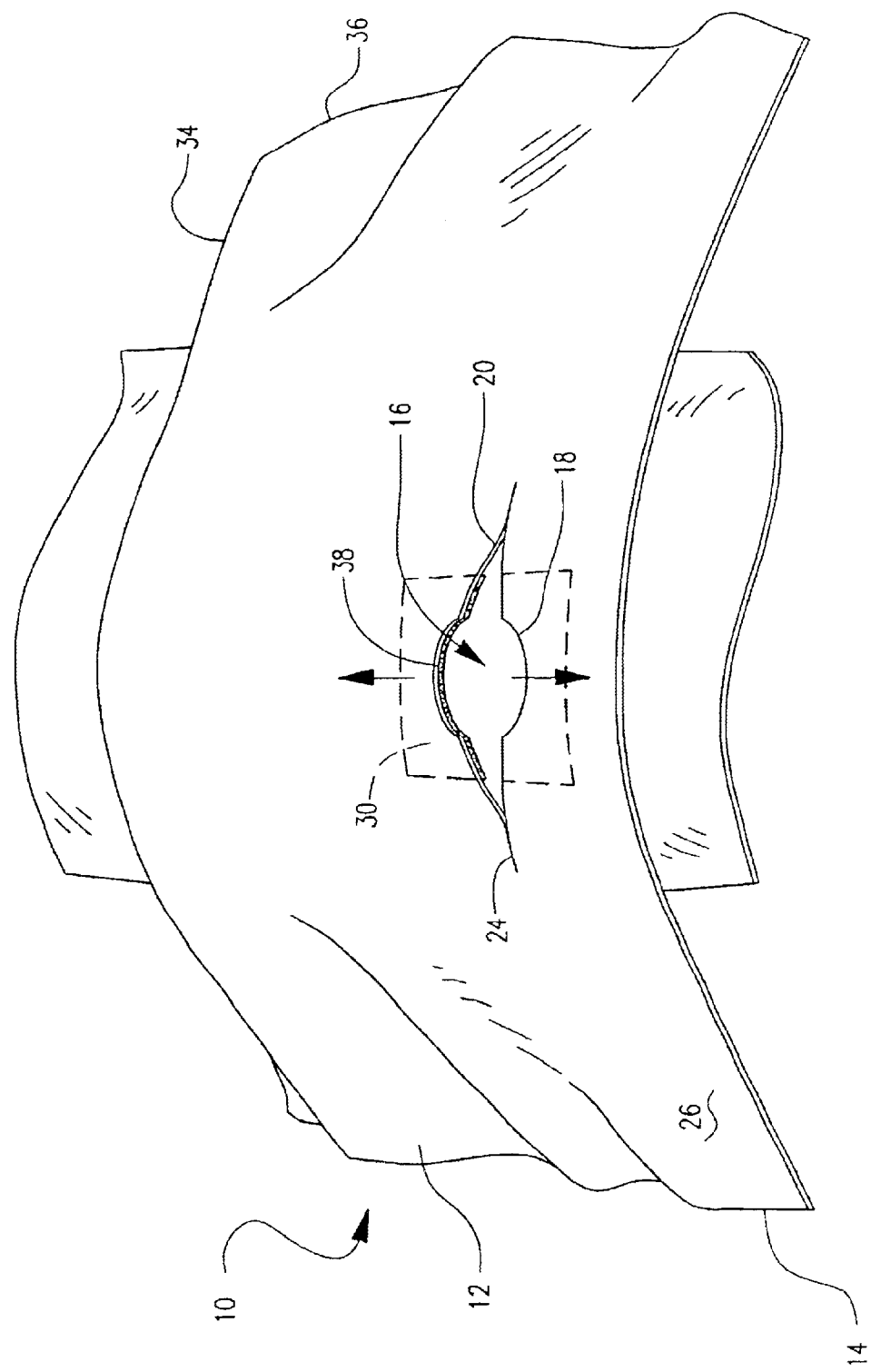

As previously noted, the aperture 16, which is preferably but not necessarily die cut from the sheet material 12, comprises a dominant portion 18 and at least one subordinate portion 20, a description of the functionality of said portions being reserved for discussion relative to FIG. 3. The dominant portion 18, as shown, resembles an oval, however other curved, symmetrical or otherwise, or non-curved (i.e., angular) configurations are contemplated, the critical consideration being structure permitting sterile access to a surgical/incision site, or more broadly, a work site. Although the shape of the dominant portion 18 of the aperture 16 may be, and is likely to be, elongate, the at least one subordinate portion 20 extending radially therefrom will substantially define an elongate aperture 16 for the drape 10.

The at least one subordinate aperture portion 20 is generally elongated (i.e., this portion has a length and width dimension, the length dimension exceeding the width dimension), being preferably slot or finger like in appearance (i.e., being delimited by parallel lines joined at their free ends, as by a uniform curve as shown, or other linkage configuration). The at least one subordinate aperture portion 20 may likewise be delimited by converging lines extending from a periphery or margin 38 of the dominant aperture portion 18 (see FIG. 3).

The subordinate aperture portion 20 generally has a minimum dimension less than the minimum dimension of the dominant aperture portion 18. Each of the opposingly paired subordinate aperture portions 20 of FIG. 1 preferably terminate within the foot print of the underlaying adhesive layer 30/release liner 32, however, as indicated by the dashed lines in FIG. 1, they need not. In other words, the subordinate aperture portion 20 may have a maximum dimension greater than the maximum dimension of the dominant portion aperture portion 18 (i.e., dashed lines of FIG. 1), however, it is preferable that the maximum dimension of the at least one subordinate aperture portion 20 not exceed that of the dominant aperture portion 18.

In the preferred embodiment, the drape 10 is generally dimensioned as a square, about 16"×16". The line of weakness 22 is positioned about 4" from an edge of the drape so as to delimit the primary 26, about 16"×12", and secondary 28, about 16"×4", drape portions. As previously noted, the aperture 16 is centrally positioned relative to the periphery 14 of the drape 10, and is generally centrally positioned with respect to the adhesive layer 30/release liner 32, typically about a 3"×4" area. The dominant aperture portion 18 is preferably dimensioned as a 1"×1.5" oval, the subordinate aperture portion 20 having a width of about 0.25" and a length range dimension of about 0.5" to 1.5"

Referring now to FIG. 3, the drape 10 of the subject invention is illustrated in an applied condition, in anticipation of a surgical procedure, for example a lasik procedure. As shown, the secondary portion 28 of the drape 10 has been removed, an expedient for such procedure, the primary drape portion 26 remaining. The line of weakness 22 offers an adaptability for the drape not otherwise available in ophthalmic drapes.

Post removal of the release liner 32, the aperture 16 of the drape 10 is aligned in a position so as to centrally overlay the work site, more particularly, the dominant aperture portion 18 is to overlay the work site. The dominant aperture portion 18 is the gateway to the work site, the at least one subordinate aperture portion 20 permitting deformation of the margins 38 of the aperture 16, more particularly the dominant aperture portion 18, in furtherance of adhering the drape and establishing the sterile field.

Application of the drape 10 includes deforming the margin 38 of the dominant aperture portion 18 such that the subordinate aperture portion 20 extending therefrom respondingly deforms so as to provide improved compliance for the dominant aperture portion 18 in and about the surgical site. In this way, and by the structures of the subject drape invention, the drape may be easily adhered to both the upper and lower margins of the eye without requiring the use of separate instruments for cutting and adjusting. No mutilation of the drape as by breaking a tear line is required so as to obtain a conforming application of the drape to the work site, furthermore, a quickly set and reliable sterile field is established with ease.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A surgical drape comprising a sheet material having a periphery and an aperture spaced apart from said periphery, said aperture having a dominant portion and at least one subordinate portion, said at least one subordinate portion a) radially extending from said dominant portion, and b) having a maximum dimension greater than a maximum dimension of said dominant portion of said aperture.

2. The surgical drape of claim 1 wherein said at least one subordinate portion of said aperture has a length and width dimension, said length dimension exceeding said width dimension.

3. The surgical drape of claim 2 wherein said at least one subordinate portion of said aperture has a minimum dimension less than a minimum dimension of said dominant portion of said aperture.

4. A surgical drape comprising a sheet material having a periphery and an aperture spaced apart from said periphery, said aperture having a dominant portion and at least one subordinate portion, said at least one subordinate portion a) radially extending from said dominant portion,
wherein said aperture is elongated, and wherein said at least one subordinate portion of said aperture comprises a slot.

5. The surgical drape of claim 4 wherein said sheet material includes an adhesive layer on a surface thereof.

6. The surgical drape of claim 5 wherein said adhesive surrounds a majority of said aperture.

7. The surgical drape of claim 6 wherein said at least one subordinate portion of said aperture is elongated.

8. The surgical drape of claim 6 wherein said at least one subordinate portion of said aperture comprises opposingly paired slots.

9. The surgical drape of claim 8 wherein said dominant portion of said aperture is round.

10. The surgical drape of claim 8 wherein said dominant portion of said aperture is angular.

11. The surgical drape of claim 9 wherein said adhesive is adjacent said dominant portion of said aperture.

12. The surgical drape of claim 11 wherein said adhesive is adjacent at least a portion of said subordinate portion of said aperture.

13. The surgical drape of claim 12 wherein said drape further includes a release liner, said release liner over laying said adhesive for selective removal therefrom.

14. The surgical drape of claim 13 wherein said aperture is centrally positioned relative to said periphery of said sheet material.

15. The surgical drape of claim 14 wherein said sheet material further includes a line of weakness, said line of weakness being substantially parallel to an axis of elongation of said at least one subordinate portion of said aperture.

16. The surgical drape of claim 15 wherein said line of weakness comprises a series of spaced apart slits.

17. The surgical drape of claim 15 wherein said line of weakness comprises a perforation.

18. The surgical drape of claim 15 wherein said line of weakness comprises a spaced apart series of punched holes.

19. The surgical drape of claim 15 wherein said line of weakness delimits primary and secondary drape portions, said primary drape portion including said aperture.

20. The surgical drape of claim 19 wherein said secondary portion is selectively removable as dictated by a select medical procedure.

21. The surgical drape of claim 19 wherein said secondary portion is selectively removable for lasik surgery.

22. In a method of applying an apertured surgical drape, the step comprising:

a. deforming a margin of a dominant aperture portion of said aperture such that a subordinate aperture portion extending from said dominant aperture portion respondingly deforms so as to provide improved compliance for said dominant aperture portion in and about a surgical site.

* * * * *